United States Patent
Farshi

(10) Patent No.: US 7,659,520 B2
(45) Date of Patent: Feb. 9, 2010

(54) ORBITRON BASED STAND-OFF EXPLOSIVES DETECTION

(75) Inventor: Esmaeil Farshi, Poway, CA (US)

(73) Assignee: NextGen, Inc., Faifax, VA (US)

( * ) Notice: Subject to any disclaimer, the term of this patent is extended or adjusted under 35 U.S.C. 154(b) by 0 days.

(21) Appl. No.: 12/330,428

(22) Filed: Dec. 8, 2008

(65) Prior Publication Data

US 2009/0146060 A1    Jun. 11, 2009

Related U.S. Application Data

(60) Provisional application No. 61/005,530, filed on Dec. 6, 2007.

(51) Int. Cl.
*G01J 1/42* (2006.01)
(52) U.S. Cl. ............... 250/393; 250/390.06; 250/494.1; 250/306; 250/374; 376/114; 376/156
(58) Field of Classification Search ............ 250/390.06, 250/494.1, 306, 374, 393; 376/114, 156
See application file for complete search history.

(56) References Cited

U.S. PATENT DOCUMENTS

| | | | | | |
|---|---|---|---|---|---|
| 4,754,196 | A | * | 6/1988 | Burke et al. | 315/5.29 |
| 4,978,889 | A | * | 12/1990 | Schumacher | 315/111.21 |
| 5,215,703 | A | * | 6/1993 | Bernardet | 376/114 |
| 5,446,288 | A | * | 8/1995 | Tumer | 250/390.05 |
| 2002/0175288 | A1 | * | 11/2002 | Taleyarkhan | 250/358.1 |
| 2005/0023479 | A1 | * | 2/2005 | Grodzins | 250/390.11 |

* cited by examiner

*Primary Examiner*—David P Porta
*Assistant Examiner*—Jessica L Eley
(74) *Attorney, Agent, or Firm*—Italia IP; James A. Italia

(57) ABSTRACT

A microwave or terahertz and neutron radiation type detector, which uses an orbitron as a radiation source. The detector may have a polarity switching apparatus to enable the orbitron to selectively change from between short wave to neutron emission functions. A highly compact and lightweight identifier of explosives and other chemicals, which may be so small and light as to be hand held, and which is effective at stand-off distances, is thereby provided.

14 Claims, 3 Drawing Sheets

ORBITRON BASED STAND-OFF EXPLOSIVES DETECTION

CROSS-REFERENCE TO RELATED APPLICATION

This application claims the benefit of the filing date under 35 USC 119(e) of the filing date of U.S. Provisional Application Ser. No. 61/005,530, filed Dec. 6, 2007 (wherein Dec. 6, 2008 fell on a Saturday), the contents of which are hereby incorporated by reference.

FIELD OF THE INVENTION

The present invention relates to detection of substances, such as explosives, using Terahertz (THz) radiation techniques, and wherein THz radiation and neutron emissions are generated by an orbitron type maser device.

BACKGROUND OF THE INVENTION

Explosives and other objectionable substances such as narcotics and polluting contaminants have long presented challenges regarding their early detection. In particular, explosives have been the subject of detection systems in recent times. Chemical detection of airborne traces of substances and imaging of apparatus which can potentially carry explosives have been developed and put into practice. However, these technologies have their limitations.

Explosives detection using THz and microwave radiation techniques is known, although this is in its infancy. Current devices tend to be large, underpowered, and have high input requirements. It is also known to provide explosives detectors which work at what has been called stand-off distances. However, devices which accomplish these functions have hereto for been large and not readily carried about. Such devices are suitable for stationary applications, such as security screening of persons entering protected facilities and premises, but are generally impractical for mobile applications wherein the apparatus is moved to different sites.

SUMMARY OF THE INVENTION

The present invention provides apparatus integrates millimeter wave, THz radiation, and fast neutron emissions technology to accomplish the above purposes in an apparatus which is sufficiently small and light as to be readily portable. This type of device is operable to detect diverse substances, such as explosives and narcotics, and also contaminants such as chemicals, petroleum, and water.

The present invention uses microwave maser type devices, in particular the orbitron, as sources of radiation which is used to identify substances. The imaging and identification system which is built around the orbitron can provide through-barrier detection and classification of explosives, chemical agents, radiological and nuclear materials, and other hazardous materials. The orbitron can be used as a neutron source by reversing polarity.

A significant aspect of the invention is adaptation of orbitron microwave maser devices to the environment of substance identity analysis.

Another significant aspect of the invention is the ability to adjust or tune resultant frequencies, which is not readily achievable in conventional short-wave devices.

Detection devices can be made as small as hand held, being about an inch in diameter and eight inches in length. This device may be powered by commercially available battery cells. Larger vehicle carried examples may be effective at one hundred meters, given an optimum antenna size.

One object of the invention is to utilize orbitrons as THz and microwave sources for stand-off detection devices.

It is an object of the invention to reduce significantly the size of THz and neutron sources so as to provide stand-off detectors that are readily portable and even hand held.

Another object is to provide THz and microwave generators that are also neutron sources.

It is an object of the invention to provide improved elements and arrangements thereof by apparatus for the purposes described which is inexpensive, dependable, and fully effective in accomplishing its intended purposes.

These and other objects of the present invention will become readily apparent upon further review of the following specification and drawings.

BRIEF DESCRIPTION OF THE DRAWINGS

Various objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION

Figure 1:
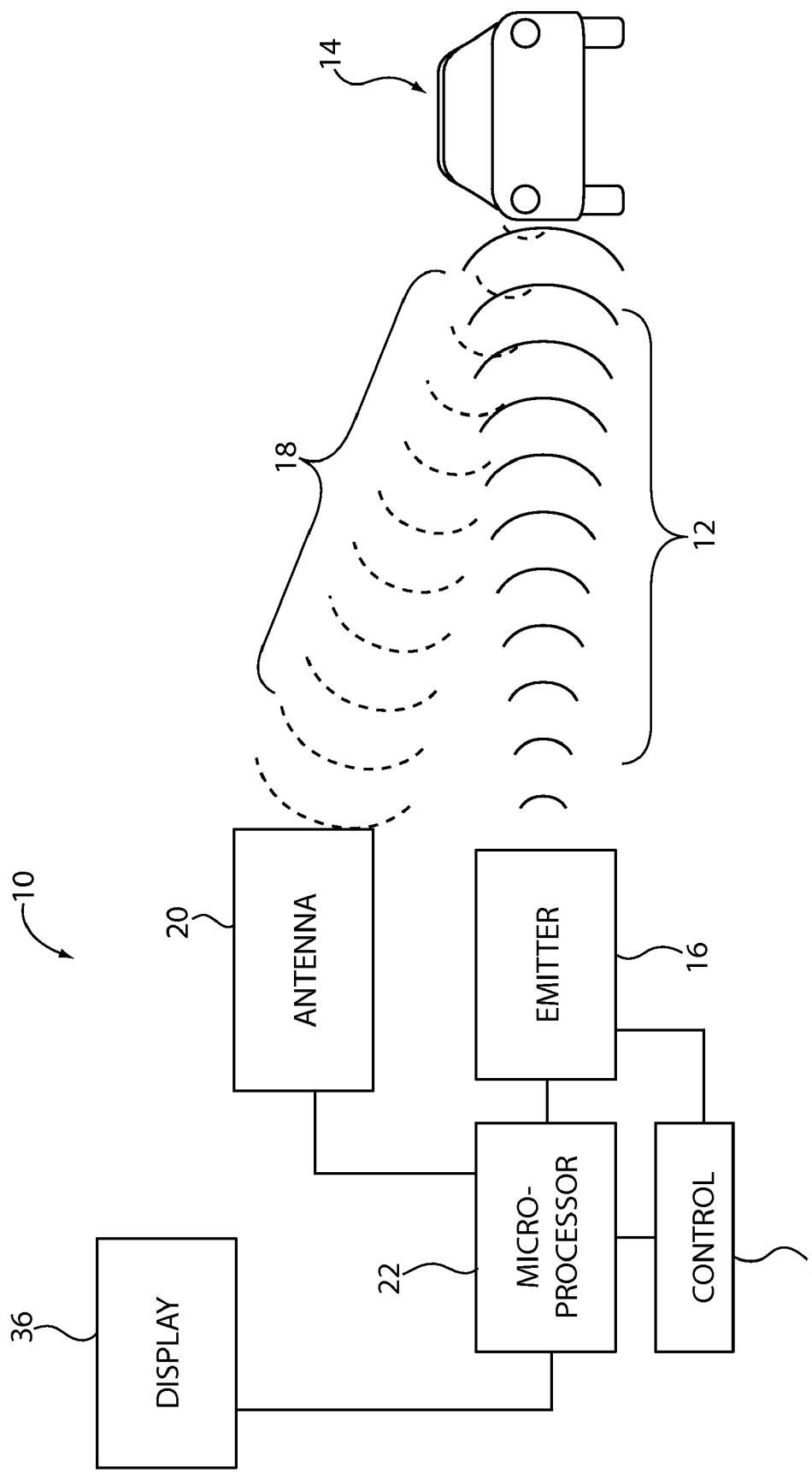
FIG. 1 is a diagrammatic, environmental side view of a detector according to at least one aspect of the invention, in use.

FIG. 1 of the drawings shows a detector 10 for identifying substances (not shown) at stand-off distances. In the example of FIG. 1, the detector 10, which operates by bombardment with radiant energy and subsequent analysis of returned energy, is seen to emit radiant energy, represented as a beam 12, towards an automobile 14 which is to be scrutinized to determine whether the automobile 14 is carrying any substances which are the subject of identification. Typically, such substances are related to national security and potential crime, such as explosives and narcotics, but may also comprise other substances of interest.

The detector 10 may comprise an emitter 16 of radiant energy in the microwave and terahertz wavelength ranges. For the purposes of this disclosure, the microwave range may be regarded as frequencies between 0.1 and 100 gigahertz (GHz), with the terahertz range being from 100 GHZ up to 10 THz. It should be made clear that there is no true formal boundary between the microwave and terahertz ranges as both technologies have asserted claim to the range of 100 to 300 GHz, and that the values set forth here are presented as a general guide rather than in the capacity of strict definition.

As is known, the advantage of these ranges is that, especially with THz frequencies, penetration of substances such as non-metallic and non-polar media is particularly effective compared to other technologies. Also, THz frequencies are held not to be harmful to human tissues or otherwise hazardous to health.

The beam 12 impinges upon the automobile 14 and upon substances contained therein. Energy originating from the beam 12 may be reflected, absorbed and reradiated, or modified and returned to the detector 10 in any fashion. Returning energy, seen as a beam 18 (shown in broken lines), impinges upon an antenna 20 which associated with the detector 10, which antenna 20 is disposed to receive radiant energy which is emitted from a substance responsively to being bombarded with radiant energy (represented as beam 12) by the emitter 16. Characteristics such as the spectral signature of the beam 18 may then be analyzed.

Illustratively, characteristics of the beam 18 may be rendered in graphic form. The graphic forms thus produced may be compared in a microprocessor 22 or in any other data processing device to be analyzed. One method of analysis is to load characteristics such as spectral signatures of known substances which are the subject of the detector 10 into a database which is associated with the microprocessor 22, and to compare the graphic form associated with the beam 18 with the preloaded characteristics. The nature of a substance being investigated by the detector 10 may be determined responsive to a match being identified between the spectral signature of the returned radiation (i.e., the beam 18) and the spectral signatures which have been previously loaded into the database.

Figure 2:
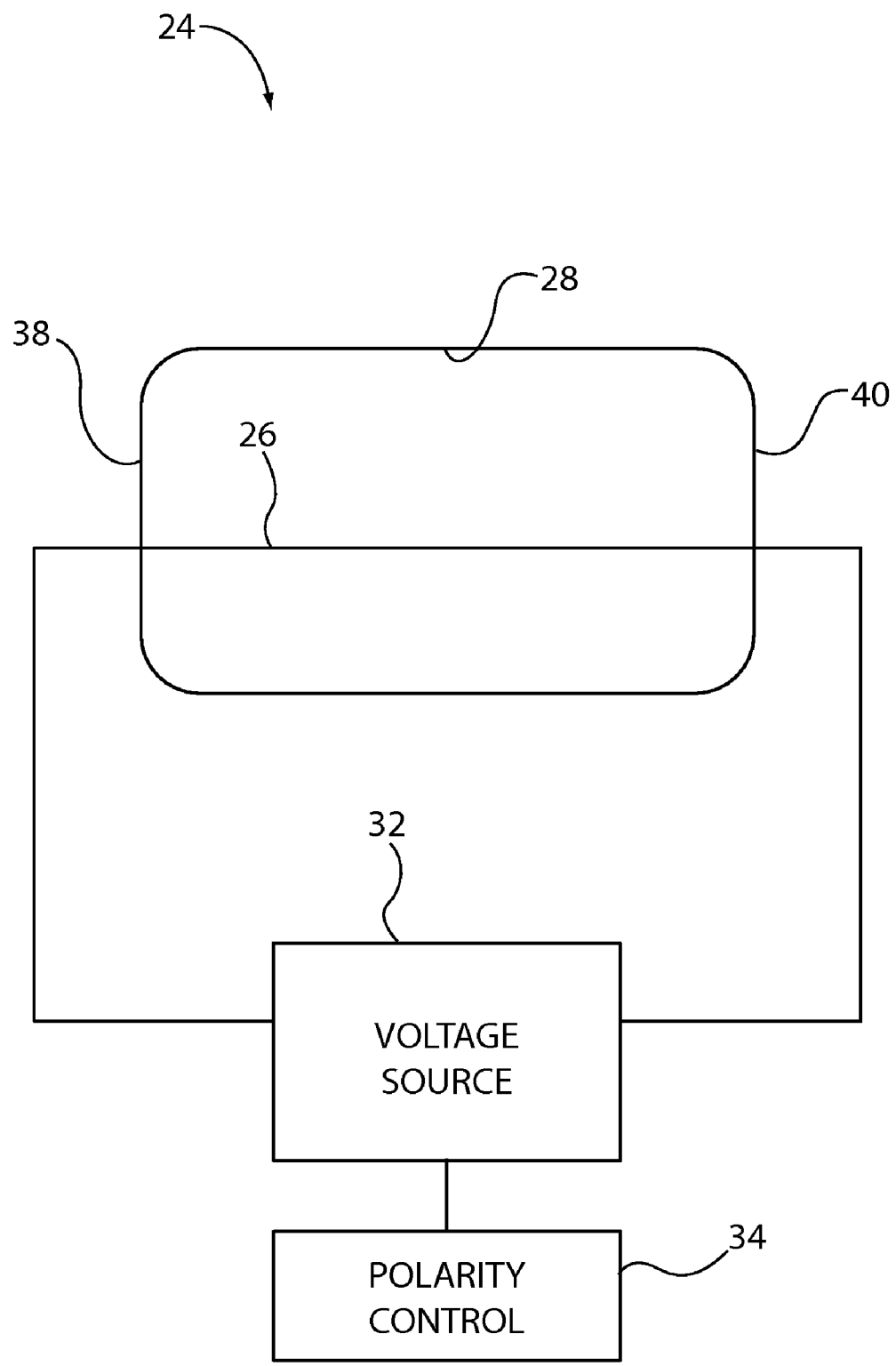
FIG. 2 is a diagrammatic representation of an orbitron arranged to form a detector according to at least one aspect of the invention.

FIG. 2 shows an arrangement wherein an orbitron 24 may be incorporated into the emitter 16. The orbitron 24 is a free electron laser like device, understanding that conceptually, there is little difference between maser and laser technology apart from the resulting frequencies. The orbitron 24 may be disposed to emit radiant energy in the terahertz and microwave wavelength ranges. Although the orbitron is a known device, its fundamental structure will be presented in order to explain modification for the purposes of the present invention. The orbitron 24 includes a central conductor 26 disposed within a surrounding microwave cavity 28. Imposition of voltage upon the central conductor 26, which may be of very small diameter, causes electrons close to its surface to orbit the central conductor 26 at high frequency, and to emit very high frequency radiation. Incorporation of an appropriate frequency control 30 (see FIG. 1), such as a bandpass filter or a frequency disperser (neither individually shown), gives the ability to tune or control emitted frequencies. Operation in the above mode is that of a microwave or THz generator.

The microwave cavity 28 may contain deuterium or a deuterium and tritium mixture. Fast neutrons may then be generated using the orbitron 24. Operation in the neutron generating mode may be accomplished by changing the polarity of the central conductor 26. This is represented in FIG. 2 as a polarity control 34 which acts on a voltage source 32 to impose appropriate voltage and polarity on the central conductor 26.

The frequency control 30, the voltage source 32, and the polarity control 34 may collectively be referred to as an excitation system disposed to impose voltages on the central conductor 26, and to generate electric fields acting on the central conductor 26. The excitation system causes electrons to orbit around the central conductor 26 and to be emitted at very high frequencies therefrom. The polarity control 34, acting in conjunction with the voltage source 32, may be regarded as a reversing arrangement disposed to selectively reverse polarity imposed on the central conductor 26, thereby selectively emitting fast neutrons from the emitter 16.

The microwave cavity 28 may comprise an electrostatic mirror or fringing field at opposed cavity ends 38, 40. This constrains orbiting electrons against travelling parallel to the central conductor.

Further information on orbitrons, such as the orbitron 24, and on THz and microwave detectors generally, may be obtained by consulting the following documents, which are hereby explicitly incorporated in their entirety herein by reference.

U.S. PATENTS

U.S. Pat. No. 4,920,313, Constant, Apr. 24, 1990
U.S. Pat. No. 6,815,683, Federici et al., Nov. 9, 2004
U.S. Pat. No. 7,105,820, Federici, Sep. 12, 2006
U.S. Pat. No. 7,319,233, Nelson, Jan. 15, 2008
U.S. Pat. No. 7,342,230, Adamski, Mar. 11, 2008
U.S. Pat. No. 7,405,409, Kearfott, Jul. 3, 2008
U.S. Pat. No. 7,430,479, Hlslin, Sep. 30, 2008
U.S. Pat. No. 7,449,695, Zimdars, Nov. 11, 2008

U.S. PUBLISHED PATENT APPLICATIONS

20060022151, Todd, Feb. 2, 2006
20060255277, Cole et al., Nov. 16, 2006
20060262876, LaDue, Nov. 23, 2006
20070114419, Bastiaans, May 24, 2007
20070263767, Brondo, Jr., Nov. 15, 2007
20080006767, Taday et al., Jan. 10, 2008
20080017806, Norris, Jan. 24, 2008
20080142722, Zillmer et al., Jun. 19, 2008

NON-PATENT LITERATURE

Alexeff, I., Radar, M., and Dyer, F. Southeastcon '88, IEEE Conference Proceedings, Apr. 11-13, 1988, pages 646-649, uses of Orbitron maser to produce millimeter and submillimeter radiation.

Todd, A. M. M., Bluem, H. P., Christina, V., Jackson, R. H., and Williams, G. P. Adv. Energy Syst., USA, appearing in "Infrared and Millimeter Waves and 13th International Conference on Terahertz Electronics", published Sep. 19-23, 2005, Volume 2, pages 497-498, describing free electron lasers to deliver THz radiation.

Again referring to FIG. 1, the microprocessor 22, by processing inputs from the antenna 20, and with appropriate programming, may provide the function of a neutron imaging arrangement. Images (not shown) thus derived may be displayed on a display 36. These images may for example show spectra of substances being analyzed or investigated by the detector 10. Alternatively, conclusions which may be drawn from the images may be displayed in the form of visible legends, symbols, and other pictorial representations (none shown) on the display 36.

A significant advantage of the invention is that the emitter 16 may comprise a sole device which is disposed to emit, selectively subject to electromagnetic excitation imposed thereto, both radiant energy in the terahertz and microwave wavelength ranges, and also, subject to appropriate manipulation of a control circuit, neutrons. The control circuit, which is disposed to vary electromagnetic excitation imposed on the emitter 16, will be understood to encompass the control frequency control 30, the voltage source 32, the polarity control 34, and other supporting and necessary apparatus regardless of whether such apparatus is set forth explicitly. The sole device may comprise an orbitron such as the orbitron 24, or another type of free electron laser type device, which can emit radiant energy and electrons selectively, relying only upon control functions to change between high frequency radiation emissions and neutron emissions.

In combination with the sole source for both high frequency short wave radiation and neutrons, and with the further observation that an orbitron does not require a magnet as do many other short wave devices, it follows that a THz detector of remarkably small size and light weight may be produced. Illustratively, a THz device (not shown, but containing an orbitron similar in function and structure to the orbitron 24 shown in FIG. 2) which is about an inch in diameter and about eight inches long, powered by commercially available battery cells, and which can produce pulsed power, may be produced. Such a device may develop 0.1 kW pulsed power and around 20 mW average power THz and microwave radiation outputs. Further, devices which are capable of reaching 1 kW pulsed power and 1 W average power can be used in the device and still retain portability (i.e. may be hand carried and hand used). Effectiveness of such a device may range between one meter and one hundred meters, depending upon variables such as desired resolution. Even with battery cell powers, a microprocessor chip, and other control circuit elements, such a device may be hand carried and used.

Figure 3:
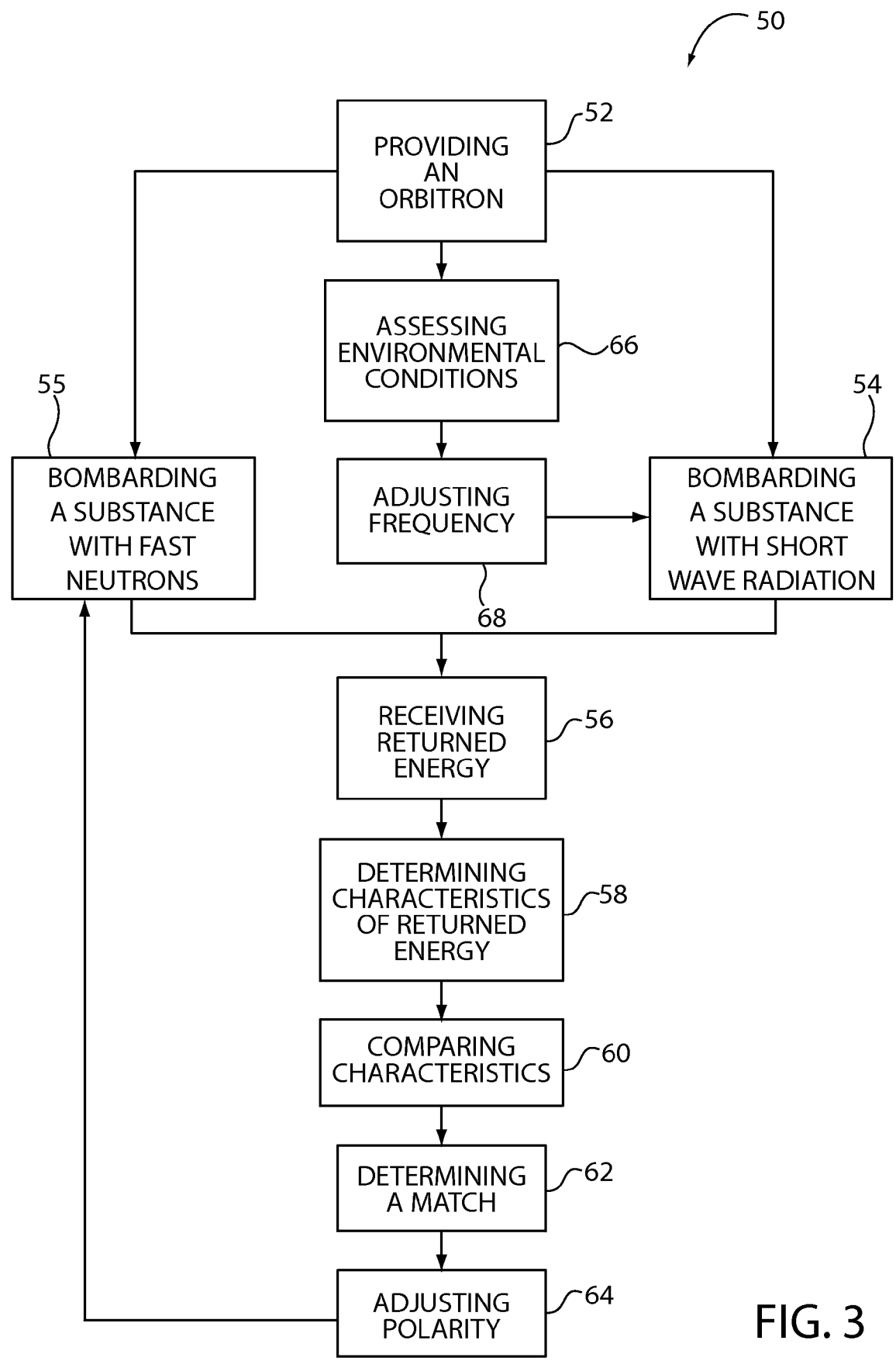
FIG. 3 is a block diagram of steps of practicing a method according to one or more aspects of the invention, and is read starting at the top.

Referring now to FIG. 3, and according to at least one further aspect, the invention may be regarded as a method 50 of identifying substances at stand-off distances. The method 50, which may employ the apparatus shown and described herein, may comprise a step 52 of providing an orbitron, such as the orbitron 24, as a radiation source of short waves including at least one of microwaves and terahertz waves, and as a source of neutrons.

The method 50 may comprise a step 54 of bombarding a substance with short wave radiation from the orbitron. As employed herein, short wave radiation will be understood to encompass microwave and THz frequency ranges.

The method 50 may comprise a step 56 of receiving energy returned from the substance which has been bombarded with short wave radiation, such as by using an antenna such as the antenna 20.

The method 50 may comprise a step 58 of determining identifying characteristics of energy returned from the substance which has been bombarded with short wave radiation. This may be accomplished for example by comparison of spectral signatures, as described above. Therefore, the method 50 may comprise a step 60 of comparing the characteristics of returned energy with spectral characteristics of, for example, known or sought substances, which have been previously been loaded into a database.

The method 50 may comprise a step 62 of determining the nature of a substance responsive to a match being identified between the characteristics of the returned energy and the characteristics which have been previously loaded into the database.

Should the step 62 of determining the nature of a substance result in a determination of presence of metal, a further step 64 may be employed, that of reversing polarity of the orbitron so as to emit fast neutrons for detection of substances enclosed within the metal. Of course, the step 64 only applies where microwave or THz radiation had been utilized in the step 62.

It should be noted that the step 64 may be employed independently of determining presence of metal. The type of emissions (short wave radiation or fast neutron) is independently selectable by adjusting polarity according to the user's desire.

The method 50 may provide for optimization or improvement of effectiveness or performance of gathering and interpreting information which may be gleaned, such as by capturing and analyzing returned energy such as the beam 18 of returned energy shown in FIG. 1. This may be done for example by assessing environmental conditions, such as by measuring humidity, rainfall, and other water content, dust, and other contaminants present in the ambient air which might affect either one or both of the beams 12 and 18. An appropriate adjustment to output frequencies of the beam 12 may responsively be made. This may be done in any suitable way. For example, should rainfall be detected by ordinary visual observation, a human operator (not shown) may enter an appropriate command which for example could merely acknowledge presence of rainfall into a microprocessor, such as the microprocessor. Responsively to such command entry, the microprocessor may execute a command which has been preloaded into the microprocessor, which command controls the excitation system of the emitter, such as the emitter 16.

Alternatively, the detector, such as the detector 10, may be provided with suitable known instruments (none shown) for measuring turbidity or other contaminants of ambient air, and automatically sending an input signal to the microprocessor, which would then issue the appropriate command to the emitter.

With this in mind, the method 50 may comprise a step 66 of assessing environmental conditions, and a step 68 of adjusting the frequency of short wave radiation being emitted from the orbitron in a manner which optimizes performance responsive to matching the frequency to the assessed environmental conditions. The point at which the steps 66 and 68 may depart from the order and arrangement shown in FIG. 3. For example, assessment of environmental conditions may be performed responsively to the step 58 of determining the characteristics (for example spectrum characteristics) of returned energy, should, for example, analysis reveal that the characteristics produce results which are degraded, impaired, or unusable.

It should be understood that due to the conceptual description presented herein, components presented in the singular may be provided in the plural. Where feasible, it would be possible to provide a single component rather than a plurality of components.

Similarly, locations of elements as presented herein are exchangeable.

Apparatus presented as continuous or discontinuous may if feasible assume the opposite.

Devices shown as assemblies may be provided as stand-alone or separate devices. Of course, the opposite is also true.

Circuitry will be understood to comprise the number of conductors, and specific connection schemes necessary to carry out the described functions, as well as supporting apparatus such as switches, relays, transducers, circuit breakers, transformers, and voltage dividers, among others, which were not specifically called out. Circuitry and any of its individual components may vary in size, number, location, and logic from that specifically shown or described herein.

While the present invention has been described in connection with what is considered the most practical and preferred embodiment, it is to be understood that the present invention is not to be limited to the disclosed arrangements, but is intended to cover various arrangements which are included within the spirit and scope of the broadest possible interpretation of the appended claims so as to encompass all modifications and equivalent arrangements which are possible.

I claim:

1. A detector for identifying substances at stand-off distances, by bombardment with radiant energy and subsequent analysis of energy returned responsively to bombardment by the substances being identified, comprising
   an emitter of radiant energy, comprising
      an orbitron disposed to emit radiant energy in the terahertz and microwave wavelength ranges, comprising a central conductor and a microwave cavity surrounding the central conductor, and an excitation system disposed to impose voltages on the central conductor, and to generate electric fields acting on the central conductor, thereby causing electrons to orbit around the central conductor and to be emitted at very high frequencies therefrom, and a reversing arrangement disposed to selectively reverse polarity imposed on the central conductor, thereby selectively emitting fast neutrons from the emitter of radiant energy; and an antenna disposed to receive radiant energy which is emitted from a substance responsively to being bombarded with radiant energy.

2. The detector of claim 1, further comprising a bandpass filter disposed to cause the orbitron to emit radiant energy at wavelengths within a continuum without continuous change in beam energy.

3. The detector of claim 1, further comprising a frequency disperser disposed to cause the orbitron to emit radiant energy at wavelengths within a continuum without continuous change in beam energy.

4. The detector of claim 1, further comprising a neutron imaging arrangement, whereby spectra of substances being analyzed by the detector may be displayed.

5. The detector of claim 1, wherein the microwave cavity has opposed ends including openings through which passes the central conductor, and wherein the detector further comprising a fringing field generator disposed at each one of the opposed ends of the microwave cavity, whereby electrons are constrained against travelling parallel to the central conductor.

6. The detector of claim 1, wherein the dimensions and weight are such that the detector may be hand carried and hand used.

7. A method of identifying substances at stand-off distances, comprising the steps of:
   providing an orbitron as a radiation source of short waves including at least one of microwaves and terahertz waves, and as a source of neutrons;
   bombarding a substance with short wave radiation from the orbitron;
   receiving energy returned from the substance which has been bombarded with short wave radiation;
   determining characteristics of energy returned from the substance which has been bombarded with short wave radiation;
   comparing the characteristics of returned energy with characteristics which have been previously been loaded into a database; and
   determining the nature of a substance responsive to a match being identified between the characteristics of the returned energy and the characteristics which have been previously loaded into the database.

8. The method of claim 7, comprising the further steps of:
   assessing environmental conditions; and
   adjusting the frequency of short wave radiation being emitted from the orbitron in a manner which optimizes performance responsive to matching the frequency to the assessed environmental conditions.

9. The method of claim 7, comprising a further step of adjusting polarity of the orbitron so as to emit fast neutrons for detection.

10. The method of claim 7, wherein should the step of determining the nature of a substance result in a determination of metal, the method further comprises a step of adjusting polarity of the orbitron so as to emit fast neutrons for detection of substances enclosed within the metal.

11. A detector for identifying substances at stand-off distances, by bombardment with radiant energy and analysis and returned energy, comprising
   an emitter of radiant energy, comprising a sole device disposed to emit selectively subject to electromagnetic excitation imposed thereto radiant energy in the terahertz and microwave wavelength ranges, which said sole device is a free electron laser type device, and also which said emitter of radiant energy is also disposed to emit neutrons, and
   a control circuit disposed to vary electromagnetic excitation imposed on the emitter of radiant energy and of neutrons.

12. The detector of claim 11, further comprising an antenna disposed to receive radiant energy which is emitted from a substance responsively to being bombarded with radiant energy emitted by the emitter of radiant energy.

13. The detector of claim 11, further comprising a neutron imaging arrangement, whereby spectra of substances being analyzed by the detector may be displayed.

14. The detector of claim 11, wherein the dimensions and weight are such that the detector may be hand carried and hand used.

* * * * *